US009149563B2

(12) United States Patent
Wei et al.

(10) Patent No.: US 9,149,563 B2
(45) Date of Patent: *Oct. 6, 2015

(54) CALCIUM PHOSPHATE/STRUCTURAL PROTEIN COMPOSITES AND METHOD OF PREPARATION THEREOF

(75) Inventors: Mei Wei, Coventry, CT (US); Haibo Qu, Secane, PA (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 769 days.

This patent is subject to a terminal disclaimer.

(21) Appl. No.: 12/265,956

(22) Filed: Nov. 6, 2008

(65) Prior Publication Data

US 2009/0130168 A1    May 21, 2009

Related U.S. Application Data

(60) Provisional application No. 60/985,681, filed on Nov. 6, 2007.

(51) Int. Cl.
| A61K 33/42 | (2006.01) |
| A61K 38/39 | (2006.01) |
| A61F 2/28 | (2006.01) |
| A61L 27/52 | (2006.01) |
| A61L 24/00 | (2006.01) |
| A61L 24/10 | (2006.01) |
| A61L 27/12 | (2006.01) |
| A61L 27/46 | (2006.01) |
| A61L 27/56 | (2006.01) |

(52) U.S. Cl.
CPC ............ *A61L 27/52* (2013.01); *A61L 24/0047* (2013.01); *A61L 24/102* (2013.01); *A61L 27/12* (2013.01); *A61L 27/46* (2013.01); *A61L 27/56* (2013.01); *A61L 2300/112* (2013.01); *A61L 2430/02* (2013.01)

(58) Field of Classification Search
None
See application file for complete search history.

(56) References Cited

U.S. PATENT DOCUMENTS

| 4,888,366 A | 12/1989 | Chu et al. |
| 6,136,369 A | 10/2000 | Leitao et al. |
| 6,187,047 B1 | 2/2001 | Kwan et al. |
| 6,887,488 B2 | 5/2005 | Cui et al. |
| 6,974,862 B2 | 12/2005 | Ringeisen et al. |
| 7,087,086 B2 | 8/2006 | Li et al. |
| 7,153,938 B2 | 12/2006 | Kikuchi et al. |
| 7,879,093 B2 | 2/2011 | Wei et al. |
| 8,003,611 B2 | 8/2011 | Kamitakahara et al. |
| 8,084,095 B2 | 12/2011 | Wei et al. |
| 2002/0018797 A1 | 2/2002 | Cui et al. |
| 2002/0018798 A1 | 2/2002 | Sewing et al. |
| 2002/0143398 A1 | 10/2002 | Osaka et al. |
| 2004/0258729 A1* | 12/2004 | Czernuszka et al. .......... 424/426 |
| 2005/0271695 A1* | 12/2005 | Kikuchi et al. ............... 424/423 |
| 2006/0204491 A1 | 9/2006 | Kakubo et al. |
| 2006/0216494 A1 | 9/2006 | Furedi-Milhofer et al. |
| 2007/0184299 A1 | 8/2007 | Wei et al. |
| 2007/0255422 A1 | 11/2007 | Wei et al. |
| 2009/0149634 A1 | 6/2009 | Shoji et al. |
| 2011/0287167 A1 | 11/2011 | Wei et al. |
| 2012/0003280 A1 | 1/2012 | Wei et al. |

FOREIGN PATENT DOCUMENTS

| EP | 1566186 A1 | 8/2005 |
| WO | 2004024201 A2 | 3/2004 |
| WO | 2007055431 A1 | 5/2007 |
| WO | 2009061887 A2 | 5/2009 |

OTHER PUBLICATIONS

Thompson, Pharmaceutics (Part I)—Spring 2004.*
Kobuko et al., Ca, P-rich layer formed on high-strength bioactive glass-ceramic A-W, J. of Biomedical Materials Research, vol. 24, p. 331-343 (1990).*
International Searching Authority, International Search Report, PCT/US2008/082586, Date of Mailing: Jul. 6, 2009, 7 pages.
International Searching Authority, Written Opnion, PCT/US2008/082586, Date of Mailing: Jul. 6, 2009, 4 pages.
Haibo Qu et al., Synthesis of Dense Collagen/Apatite Composites Using a Biomimetic Method, Journal of the American Ceramic Societyvol. 91 Issue 10, pp. 3211-3215Published Online: Aug. 26, 2008.
H. Qu and M. Wei, "The Effect of Temperature and Initial pH on Biomimetic Apatite Coating", Journal of Biomedical Materials Research: 87B, 204-212 (2008).
Yun Chen et al., Composite Coating of Bonelike Apatite Particles and Collagen Fibers on Poly L-Lactic Acid Formed Through an Accelerated Biomimetic Coprecipitation Process, 315-322, 2006.
Cai Yanli et al., Formation of bonelike apatite-collagen composite coating on the surface of NiTi shape memory alloy, Scripta Materialia 54 (2006) 89-92.
Yuwei Fan et al., A composite coating by electrolysis-induced collagen self-assembly and calcium phosphate mineralization, Biomaterials 26 (2005) 1623-1632.
Yun Chen et al., PLLA scaffolds with biomimetic apatite coating and biomimetic apatite/collagen composite coating to enhance osteoblast-like cells attachment and activity, Surface & Coatings Technology 201 (2006) 575-580.

(Continued)

*Primary Examiner* — Kevin S Orwig
(74) *Attorney, Agent, or Firm* — Cantor Colburn LLP

(57) ABSTRACT

Ceramic/structural protein composite scaffolds and their preparation in a simple one-step process are shown.

8 Claims, No Drawings

(56) References Cited

OTHER PUBLICATIONS

Jerome Gross et al., The Heat Precipitation of Collagen from Neutral Salt Solutions: Some Rate-Regulating Factors, The Journal of Biological Chemistry, vol. 233, No. 2, 355-360, Jan. 16, 1958.
Haibo Qu et al., Improvement of Bonding Strength Between Biomimetic Apatite Coating and Substrates, Part B: Applied Biomaterials: vol. 84B Issue 2, pp. 436-443 2007.
Haibo Qu et al., The Effect of Initial pH on Morphology of Biomimetic Apatite Coating, Key Engineering Materials vols. 330-332 (2007), pp. 757-760.
Kim et al., Bonding strength of bonelike apatite layer to Ti metal substrate, Journal of Biomedical Materials Research 1997, 38(2): 121-127.
W. Zhang et al., Hierarchical Self-Assembly of Nano-Fibrils in Mineralized Collagen, Chem. Mater. 2003, 15, 3221.
Barrere et al., Nucleation of biomimetic Ca-P coatings on Ti6A14V from a SBF x 5 solution: influence of magnesium, Biomaterials 23 (2002) 2211-2220.
Barrere et al., Influence of ionic strength and carbonate on the Ca-P coating formation from SBFx5 solution, Biomaterials 23 (2002) 1921-1930.
Yu et al., Incorporation of Bovine Serum Albumin into Biomimetic Coatings on Titanium with High Loading Efficacy and Its Release Behavior, Journal of Materials Science, Materials in Medicine, DOI.
U.S. Appl. No. 11/619,659, filed Jan. 4, 2007.
U.S. Appl. No. 12/265,979, filed Nov. 6, 2008.
International Search Report; International Application No. PCT/US2008/082616; International Filing Date Jun. 11, 2008; 7 pages.
Written Opinion of the International Searching Authority; International Search Report; International Application No. PCT/US2008/082616; International Filing Date Jun. 11, 2008; 8 pages.
Yu et al., "Incorporation of bovine serum albumin into biomimetic coatings on titanium with high loading efficacy and its release behavior", J. Mater Sci: Mater. Med. 20, 2008, pp. 287-294.
Doi et al., "Osteonectin Inhibiting De Novo Formation of Apatite in the Presence of Collagen", Calcif Tissue Int. (1989) 44:200-208.
Bradt et al.; "Biomimetic Mineralization of Collagen by Combined Fibril Assembly and Calcium Phosphate Formation"; Chem. Mater.; 11; pp. 2694-2701; (1999).
Chen et al., "Composite Coating of Bonelike Apatite Particles and Collagen Fibers on Poly L-Lactic Acid Formed Through an Accelerated Biomimetic Coprecipitation Process", Wiley Periodicals, Inc., 2006, pp. 315-322.
Chen et al., Abstract "Biomimetic coating of apatite/collagen composite on Poly L-Lactic Acid facilitates cell seeding", Engineering in Medicine and Biology Society, 2006, 1 page.
Chen et al., Biomimetic coating of apatite/collagen composite on Poly L-lactic Acid facilities cell seeding. Conf. Proc. IEEE Eng. Med. Biol. Soc. 2005, vol. 4, pp. 4087-4090, Abstract, 1 page.
Deville, Sylvain; "Freeze-Casting of Porous Biomaterials: Structure, Properties and Opportunities"; Materials; 3; ppp 1913-1927; (2010).
International Search Report and Written Opinion: International Application No. PCT/US2013/033443; International Filing Date Mar. 22, 2013; Date of Mailing Jul. 9, 2013; 13 pages.
Landi et al. "Porous Hydroxyapatite/Gelatine Scaffolds with Ice-Designed Channel-Like Porosity for Biomedical Applications"; Acta Biomaterialia; 4; pp. 1620-1626; (2008).
Zhang et al.; "Hierarchical Self-Assembly of Nano-Fibrils in Mineralized Collagen"; Chem. Mater.; 15; pp. 3221-3226; (2003).

* cited by examiner

CALCIUM PHOSPHATE/STRUCTURAL PROTEIN COMPOSITES AND METHOD OF PREPARATION THEREOF

CROSS REFERENCE TO RELATED APPLICATION

This application claims the benefit of U.S. Provisional Application Ser. No. 60/985,681 filed Nov. 6, 2007, which is hereby incorporated by reference in its entirety.

STATEMENT REGARDING FEDERALLY SPONSORED RESEARCH

The U.S. Government has certain rights in this invention pursuant to Grant No. DMI 0500269 awarded by the National Science Foundation.

BACKGROUND OF INVENTION

Implantable medical devices, such as orthopedic and dental prostheses, can be made more permanent if the interface between the existing bone and the device contains some natural bone growth to knit the two components together. Such ingrowth has advantages over the use of bone cement, both in terms of stability and permanency.

"Bioactive" coatings on implantable medical devices allow for the ingrowth of natural bone into and around the device, forming chemical bonds between the device and natural bone. Bone is composed of substituted apatite crystals in an abundant collagen network. Type I collagen is the major protein of bone tissue, making up about thirty percent of the weight of bone. It has been shown that apatite crystals can grow and bond to collagen fibrils, and prepared apatite/collagen composites have been shown to promote direct bone apposition.

In addition to coatings, other materials made from apatite are used for bone repair and replacement. The cross-linked apatite/collagen porous scaffold materials have been studied for their excellent compatibility with human bone. Several approaches to preparing an apatite/collagen composite scaffold have been studied, but have exhibited drawbacks with respect to variable porosity of the composite.

One known approach is to prepare a composite material containing protein osteoinductive factor, mineral (mixture of hydroxyapatite and tricalcium phosphate) and collagen in a water suspension by a mechanical mixing means.

Another approach is by mixing insoluble collagen with calcium chloride and tribasic sodium phosphate at pH around 11.0. However, insoluble collagen was used to directly mix with apatite to form into composites, which may render an inhomogeneous apatite/collagen composite.

Finally, it is known to prepare an apatite/collagen composite using soluble collagen, phosphoric acid and calcium salt. Instead of forming apatite/collagen composite in one step, once the soluble collagen, phosphoric acid and calcium salt mix, the slurry-like mixture is freeze-dried. The gelation of collagen is carried out after freeze-drying apatite/collagen composite at a pH around 11.0. After gelation of collagen, the apatite/collagen composite is freeze-dried again to synthesis the apatite/collagen scaffold. Then the apatite/collagen scaffold is cross-linked and cleaned. This process requires two freeze-drying procedures and two cleaning procedures to form apatite/collagen composite scaffolds.

None of the above processes addresses the variable porosity of apatite/collagen scaffold, a factor that is important to control the regeneration of new bone tissue.

There remains a need in the art for improved apatite composite scaffolds, as well as improved processes to prepare porosity controllable apatite composite scaffolds.

BRIEF DESCRIPTION OF THE INVENTION

In one embodiment, a method of forming a composite scaffold comprises forming an aqueous scaffold system comprising a structural protein, a weak acid, water, $Ca^{2+}$, $HPO_4^{2-}$, a buffer system, and optionally one or more of $Mg^{2+}$, $Na^+$, $K^+$, $Cl^-$, $SO_4^{2-}$; or $HCO_3^-$; wherein the aqueous scaffold system has an initial pH of about 6.5 to about 8.0; placing the aqueous system in container; sealing the container; isolating a gel; and freeze-drying the gel to form a composite scaffold.

In another embodiment, an implantable medical device comprises a composite scaffold prepared by the process comprising forming an aqueous scaffold system comprising a structural protein, a weak acid, water, $Ca^{2+}$, $HPO_4^{2-}$, a buffer system, and optionally one or more of $Mg^{2+}$, $Na^+$, $K^+$, $Cl^-$, $SO_4^{2-}$; or $HCO_3^-$; wherein the aqueous scaffold system has an initial pH of about 6.5 to about 8.0; placing the aqueous scaffold system in container; sealing the container; allowing a gel to form; isolating the gel; and freeze-drying the gel to form a composite scaffold.

Also disclosed herein are composite scaffolds prepared by the processes, as well as uses for composite scaffolds.

DETAILED DESCRIPTION

Disclosed herein are methods of forming ceramic/structural protein composite scaffolds in a simple one-step process; composite scaffolds prepared therefrom; and articles prepared therefrom. With the disclosed method, a controllable structural protein content apatite/structural protein scaffold can be formed.

Disclosed herein is a method to prepare ceramic/structural protein composite scaffolds in a convenient, one-step process. The resulting scaffold is a porous composite containing up to about ninety weight percent incorporated structural protein. The method involves preparing an aqueous scaffold system containing water, $Ca^{2+}$, $HPO_4^{2-}$ structural protein (e.g., collagen type I and the like), a weak acid (eg. acetic acid, and the like) and a buffer system; and optionally one or more of the following ions: $Mg^{2+}$, $Na^+$, $K^+$, $Cl^-$, $SO_4^{2-}$, $HCO_3^-$; wherein the aqueous scaffold system has an initial pH of about 6.50 to about 8.00. The aqueous scaffold system is allowed to stand, for example at a temperature of about 20° C. to about 45° C., to form a composite gel, the gel is optionally crosslinked, isolated, mixed with water and freeze-dried to form a porous ceramic/structural protein composite scaffold. Prior to freeze drying, the mixture can be placed in a mold.

The structural protein used to prepare the scaffold can be any known structural protein such as collagens, elastin, and keratins, specifically collagen, and more specifically soluble collagen Types I, II, III, and V, and yet more specifically collagen Type I. As used herein, soluble collagen means "collagen molecules or microfibrils which are soluble in an aqueous solution".

There is no particular limitation as to the source of the structural protein. The structural protein may be obtained from commercial sources or extracted from natural sources using procedures well known in the art.

When collagen Type I is used as the structural protein, the collagen gelation and apatite precipitation happen simultaneously after incubation for about 2 to about 8 hours. The gel-like composite is then cross-linked, cleaned with pure water and freeze-dried to form apatite/collagen scaffold with varying porosity depending upon the amount of water contained in the initial scaffold. The scaffold's collagen to apatite ratio is controlled by the initial collagen concentration of the aqueous scaffold system.

The amount of structural protein (e.g., collagen) in the resulting scaffold can be about 1 to about 90 weight percent based on the total weight of the scaffold, specifically about 10 to about 80 weight percent, more specifically about 25 to about 65 weight percent, and yet more specifically about 40 to about 50 weight percent.

The aqueous scaffold system generally comprises the following inorganic ions: $Ca^{2+}$ and $HPO_4^{2-}$; and optionally one or more of the following ions: $Mg^{2+}$, $Na^+$, $K^+$, $Cl^-$, $SO_4^{2-}$, $HCO_3^-$. The aqueous system can be prepared by dissolving in an aqueous solvent salts that when disassociated will result in the particular ions $Ca^{2+}$, $Mg^{2+}$, $Na^+$, $K^+$, $Cl^-$, $SO_4^{2-}$, $HPO_4^{2-}$ and $HCO_3^-$. The aqueous solvent can be deionized and purified water. Exemplary salts include those that result in an aqueous solution of the desired ions, for example, alkali metal halides, alkaline earth metal halides, alkali metal hydrogen carbonates, alkali metal phosphates, and alkali metal sulfates. Specific salts include, NaCl, KCl, $K_2HPO_4$, $MgCl_2$, $Na_2SO_4$, $CaCl_2$ and $NaHCO_3$.

The particular concentrations of each of the above-described ions initially present in the aqueous system can be as follows:

$Ca^{2+}$ at about 0.1 to about 15.0 mM, specifically about 0.5 to about 10.0 mM, and more specifically about 1.0 to about 2.0 mM;

$Mg^{2+}$ at about 0 to about 5.0 mM, specifically about 0.05 to about 1.0 mM, and more specifically about 0.2 to about 0.4 mM;

$Na^+$ at about 0 to about 300.0 mM, specifically about 5.0 to about 100.0 mM, and more specifically about 20.0 to about 50.0 mM;

$K^+$ at about 0 to about 10.0 mM, specifically about 0.1 to about 5.0 mM, and more specifically about 1.0 to about 2.0 mM;

$Cl^-$ at about 0 to about 300.0 mM, specifically about 5.0 to about 100.0] mM, and more specifically about 20.0 to about 50.0 mM;

$SO_4^{2-}$ at about 0 to about 2.0 mM, specifically about 0.1 to about 1.5 mM, and more specifically about 0.4 to about 0.6 mM;

$HPO_4^{2-}$ at about 0.05 to about 10.0 mM, specifically about 0.1 to about 3.0 mM, and more specifically about 0.5 to about 1.0 mM; and $HCO_{3-}$ at about 0 to about 30.0 mM, specifically about 0.5 to about 10.0 mM, and more specifically about 2.0 to about 5.0 mM.

An additional component present in the aqueous scaffold system is a buffer system. The buffer system can contain HEPES (4-(2-hydroxyethyl)-1-piperazineethanesulfonic acid or N-2-hydroxyethylpiperazine-N'-2-ethanesulfonic acid; Molecular formula: $C_8H_{17}N_2SO_3$; CAS No: 7365-45-9) and an alkali metal hydrogen carbonate (e.g. $NaHCO_3$, KHCO3, etc.) which are added to the aqueous scaffold system in amounts to substantially stabilize the aqueous system. The concentration of HEPES present in the aqueous scaffold system can be at about 5.0 grams per liter (g/L) to about 80.0 g/L, specifically about 10.0 g/L to about 60.0 g/L, and more specifically about 12.0 g/L to about 48.0 g/L.

Additional buffer systems may include tris-hydroxymethyl aminomethan (TRIS), HEPES salts, piperazine-1,4-bis(2-ethanesulfonic acid) (PIPES), PIPES salts, combinations of the foregoing with an alkali metal carbonate, and combinations thereof.

The aqueous scaffold system may optionally contain additional ionic components such as silicate, strontium, zinc, silver, fluoride, combinations thereof, and the like.

The weak acid present in the aqueous scaffold system can be any acid with a pKa of about 3.5 to about 5.5. Exemplary acids include organic acids, specifically alkyl carboxylic acids such as acetic acid, propionic acid, and the like.

The aqueous scaffold system can have an initial pH of about 6.5 to about 8.0, specifically about 7.0 to about 7.5.

The temperature of during the process to prepare the scaffold can be about 15 to about 50° C., specifically about 20 to about 45° C., and yet more specifically about 25 to about 40° C.

The incubation time for preparing the composite gel can be about 0.5 to about 10 hours, specifically about 1.0 to about 9 hours, and yet more specifically about 2.0 to about 8.0 hours.

Various crosslinking agents, such as a carbodiimide, can be used to crosslink the collagen. Exemplary crosslinking agents include glutaraldehyde, 1-ethyl-3-[3-dimethylaminopropyl] carbodiimide hydrochloride optionally in combination with N-hydroxysuccinimide or N-hydroxysulfosuccinimide; dimethyl suberimidate, bis(sulfosuccinimidyl)suberate ($BS^3$), 3,3'-dithiobis(sulfosuccinimidylpropionate) (DTSSP), sulfo-succinimidyl-4-(N-maleimidomethyl)cyclohexane-1-carboxylate (Sulfo-SMCC), dithiobis(succinimidyl)propionate (DSP), sulfosuccinimidyl 6-(3'-[2-pyridyldithio]-propionamido)hexanoate, and the like. The amount of crosslinking agent used can be about 0.1 to about 0.4 M, specifically about 0.2 to about 0.3 M.

In one embodiment, a method of forming a composite scaffold comprises forming an aqueous scaffold system comprising a structural protein, a weak acid, water, $Ca^{2+}$, $Mg^{2+}$, $Na^+$, $K^+$, $Cl^-$, $SO_4^{2-}$, $HPO_4^{2-}$, $HCO_3^-$ and a buffer system, wherein the aqueous scaffold system has an initial pH of about 6.5 to about 8.0; placing the aqueous system in container; sealing the container; allowing a gel to form; isolating the gel; and freeze-drying the gel to form a composite scaffold. In another embodiment, the method of forming a composite scaffold further comprises molding the gel prior to freeze-drying.

The resulting ceramic is generally a bone-like apatite, but can also be other types of calcium phosphate. Exemplary calcium phosphate minerals include $Ca_5(PO_4)_{3-x}(OH)_{1-y}(CO_3)_{x+y}$, $Ca_5(PO_4)_3(OH)$, $Ca_3(PO_4)_2$, $CaHPO_4$, $Ca(H_2PO_4)_2$, and the like.

The scaffolds can be used to prepare medical, surgical, reconstructive, orthopedic, orthodontic, prosthodontic, endodontic or dental devices, implants, appliances, or a component thereof.

EXAMPLES

Example 1

Apatite/collagen Composite: Scaffold

A soluble collagen solution was prepared from extraction of three rat tails in 1 L solution (~1.5 g/L) according to the following procedure. Type I collagen was extracted from rat tail tendon as previously described W. Zhang, S. S. Liao, F. Z. Cui, Chem. Mater. 2003, 15, 3221. The rat tail tendon was soaked in 0.5 M acetic acid for 3-4 days at 4° C. The solution was centrifuged at 10,000 rpm at 4° C. for 15 minutes and filtered with No. 1 filter paper to remove the insoluble components. NaCl (5% wt %) was added to induce precipitation of collagen, and the precipitates were collected by centrifuging at 10,000 rpm for 15 minutes at 4° C. Collagen was then dissolved in 0.5 M acetic acid to form a collagen solution. The collagen solution was added to an aqueous system containing $Ca^{2+}$ and $HPO_4^{2-}$, $Na^+$, $K^+$, $Mg^{2+}$, $Cl^-$, $HCO_3^-$, $SO_4^{2-}$ and acetic acid; prepared from NaCl, $NaHCO_3$, $Na_2CO_3$, KCl, $K_2HPO_4\cdot 3H_2O$, $MgCl_2\cdot H_2O$, HEPES, $CaCl_2$, $Na_2SO_4$, and glacial acetic acid. The amount of inorganic salts used in the aqueous system was varied to explore the apatite/collagen ratio in the final composite (Table 3). The initial pH of the collagen containing aqueous system was adjusted to 7.5 using 5M NaOH.

TABLE 3

The ion concentrations of collagen containing aqueous system

| Ions | Sample 1 | Sample 2 | Sample 3 | Sample 4 |
|---|---|---|---|---|
| $Na^+$ | 109.5 mM | 43.6 mM | 21.8 mM | 10.9 mM |
| $K^+$ | 6.0 mM | 2.4 mM | 1.2 mM | 0.6 mM |
| $Mg^{2+}$ | 1.5 mM | 0.6 mM | 0.3 mM | 0.15 mM |
| $Ca^{2+}$ | 7.5 mM | 3 mM | 1.5 mM | 0.75 mM |
| $Cl^-$ | 110.0 mM | 44 mM | 22 mM | 11 mM |
| $HCO_3^-$ | 17.5 mM | 7 mM | 3.5 mM | 1.75 mM |
| $HPO_4^{2-}$ | 3.0 mM | 1.2 mM | 0.6 mM | 0.3 mM |
| Collagen | ~1.5 g/L | ~1.5 g/L | ~1.5 g/L | ~1.5 g/L |

Fifty milliliters of collagen containing aqueous system was placed in a sealed 100 ml bottle and allowed to form an apatite/collagen composite. The composite formation process is carried out at 40° C. After 4 hours, the collagen started to form hydrogel-like material. Five ml of glutaraldehyde is then added to further cross-link the collagen. After one-hour for the crosslinking, the apatite/collagen hydrogel is collected and rinsed with 50 ml deionized water four times using centrifuge (7000-12000 rpm). The apatite/collagen composite is then transferred into a cylinder mold and mixed with water. The porosity of the scaffold can be controlled by the amount of water added at this point in the process. The more water is present, the more porous the scaffold becomes. After that, the mixture was freeze-dried to obtain a porous apatite/collagen scaffold.

The resulting composite was then characterized by thermogravimetric analysis (TGA). The analysis revealed that the collagen content of the resulting composite was prepared in a controlled manner (20%-90 wt %) (Table 4).

TABLE 4

Collagen content in apatite/collagen composite materials (calculated using TGA)

| Specimen | Sample 1 | Sample 2 | Sample 3 | Sample 4 |
|---|---|---|---|---|
| Collagen content (wt %) | 22 | 36 | 70 | 87 |

Example 2

In Vitro Cell Culture Test

An apatite/collagen composite scaffold was prepared by extracting Type I collagen from rat tails and dissolved in 0.5 M acetic acid. The components used to make the aqueous system, including $NaCl$, $CaCl_2$, $K_2HPO_4$, $MgCl_2$, $NaHCO_3$ and HEPES, were added to the collagen solution (approximately 1.5 g/L) to prepare collagen containing aqueous system. The concentrations of these components are listed in Table 5. The initial pH of the solution was adjusted to 7.0 at 40° C. using dilute HCl or NaOH. The solution was aged for 4 hours to allow co-precipitation of apatite nanoparticles and collagen fibers in the solution. After aging, the precipitates were collected and freeze-dried to form a scaffold. The scaffold is crosslinked using 2 w/v % 1-ethyl-3-(3-dimethylaminopropyl) carbodiimide hydrochloride (EDC) at 4° C. for 24 hours, then rinsed and freeze-dried to attain the final scaffold.

TABLE 5

| Component | g/50 mL |
|---|---|
| NaCl | 0.2701 |
| $CaCl_2$ | 0.0440 |
| $K_2HPO_4\cdot 3H_2O$ | 0.0360 |
| $MgCl_2\cdot 6H_2O$ | 0.0155 |
| HEPES | 0.6000 |
| $NaHCO_3$ | 0.0736 |

The scaffold was cut into 5 millimeter (mm) discs, and seeded with MC3T3 cells. The cell seeding density was $1.6\times 10^5$ cells/scaffold. After five days of incubation in Dulbecco's Modified Eagle's Medium (DMEM) containing 10% fetal calf serum (FCS), penicillin (100 units/ml), streptomycin (100 μg/ml), and non-essential amino acids (100 μM), the cell seeded scaffolds were harvested, embedded, stained with hematoxylin, and frozen-sectioned at a thickness of 10 μm. The stained samples were then observed under light microscope. Microscopic examination revealed many cells have penetrated into the scaffold, suggesting that the scaffold supports cell attachment.

Example 3

In Vivo Test

Five day old mouse calvaria digest cells, a rich source of osteogenic progenitor cells, were harvested from a litter derived from a homozygous Col3.6GFP father and a non-transgenic mother. All the off spring carries one copy of the Col3.6GFP transgene, which is inactive at the time the cells are harvested. The cells were loaded onto the surface of an apatite/collagen composite scaffold at a density of $1.0\times 10^6$ cells/scaffold. The apatite/collagen composite scaffold was prepared similarly to Example 2, except the collagen concentration was approximately 1.0 g/L. The scaffold was punched into 3.5 mm diameter discs with a thickness of approximately 1 mm. A mouse calvaria model was used with two 3.5 mm defects created at each side of the suture line at the calvaria site. One positive control and one apatite/collagen scaffold were implanted. The implantation period was 28 days. After harvest, the implants were embedded and frozen-sectioned. Adjacent images were obtained from a Zeiss Axiovert and AxioObserver work station and tiled together to reproduce a full-size image of the bone section. It was found that the apatite/collagen composite scaffold supports bone formation. The new bone formation was mainly contributed by donor cells.

The terms "a" and "an" herein do not denote a limitation of quantity, but rather denote the presence of at least one of the referenced item. The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 wt %, or, more specifically, about 5 wt % to about 20 wt %", is inclusive of the endpoints and all intermediate values of the ranges of "about 5 wt % to about 25 wt %," etc).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of forming a composite scaffold, the method comprising:
    forming an aqueous scaffold system comprising a structural protein, a weak acid, water, $Ca^{2+}$, $HPO_4^{2-}$, $Mg^{2+}$, $Na^+$, $K^+$, $Cl^-$, $SO_4^{2-}$, $HCO_3^-$, and a buffer system, wherein the aqueous scaffold system has an initial pH of 6.5 to 8.0 and wherein in the aqueous scaffold system:
    the structural protein is collagen Type I, II, III, or V present in an amount of about 0.1 g/L to about 5.0 g/L
    the $Ca^{2+}$ is present in an amount of about 3.0 to about 15.0 mM,
    the $HPO_4^{2-}$ is present in an amount of about 3.0 to about 10.0 mM
    the $Mg^{2+}$ is present in an amount of about 0.05 to about 5.0 mM,
    the $Na^+$ is present in an amount of about 5.0 to about 300.0 mM,
    the $K^+$ is present in an amount of about 0.1 to about 10.0 mM,
    the $Cl^-$ is present in an amount of about 5.0 to about 300.0 mM,
    the $SO_4^{2-}$ is present in an amount of about 0 to about 2.0 mM,
    the $HCO_3^-$ is present in an amount of about 0.5 to about 30.0 mM;
    forming a calcium phosphate-structural protein composite by the simultaneous co-precipitation of calcium phosphate and structural protein from the aqueous scaffold system, wherein the calcium phosphate is precipitated on the surface of fibers of the structural protein;
    isolating the calcium phosphate-structural protein composite;
    freeze-drying the isolated calcium phosphate-structural protein composite to form a calcium phosphate-structural protein composite scaffold.

2. The method of claim 1, wherein the collagen content in the composite scaffold is about 10 to about 90 weight percent based on the total weight of the composite scaffold.

3. The method of claim 1, further comprising molding the isolated calcium phosphate-structural protein composite prior to freeze-drying.

4. The method of claim 1, wherein the weak acid has a pKa of about 3.5 to about 5.5.

5. The method of claim 1, further comprising adding a crosslinking agent to crosslink the calcium phosphate-structural protein composite prior to isolating.

6. The method of claim 1, further comprising placing the aqueous scaffold system in a container wherein the container is sealed prior to allowing the calcium phosphate-structural protein composite to form.

7. The method of claim 1, wherein the collagen content in the composite scaffold is 50 to about 90 weight percent based on the total weight of the composite scaffold.

8. A method of forming a composite scaffold, the method consisting of:
    forming an aqueous scaffold system comprising a structural protein, a weak acid, water, $Ca^{2+}$, $HPO_4^{2-}$, $Mg^{2+}$, $Na^+$, $K^+$, $Cl^-$, $SO_4^{2-}$, $HCO_3^-$, and a buffer system, wherein the aqueous scaffold system has an initial pH of 6.5 to 8.0 and wherein in the aqueous scaffold system:
    the structural protein is collagen Type I, II, III, or V present in an amount of about 0.1 g/L to about 5.0 g/L
    the $Ca^{2+}$ is present in an amount of about 3.0 to about 15.0 mM,
    the $HPO_4^{2-}$ is present in an amount of about 3.0 to about 10.0 mM
    the $Mg^{2+}$ is present in an amount of about 0.05 to about 5.0 mM,
    the $Na^+$ is present in an amount of about 5.0 to about 300.0 mM,
    the $K^+$ is present in an amount of about 0.1 to about 10.0 mM,
    the $Cl^-$ is present in an amount of about 5.0 to about 300.0 mM,
    the $SO_4^{2-}$ is present in an amount of about 0 to about 2.0 mM,
    the $HCO_3^-$ is present in an amount of about 0.5 to about 30.0 mM;
    forming a calcium phosphate-structural protein composite by the simultaneous co-precipitation of calcium phosphate and structural protein from the aqueous scaffold system, wherein the calcium phosphate is precipitated on the surface of fibers of the structural protein;
    optionally adding a crosslinking agent to crosslink the calcium phosphate-structural protein composite;
    isolating the calcium phosphate-structural protein composite;
    optionally molding the isolated calcium phosphate-structural protein composite; and
    freeze-drying the isolated calcium phosphate-structural protein composite to form a calcium phosphate-structural protein composite scaffold.

* * * * *